Figure 1A:
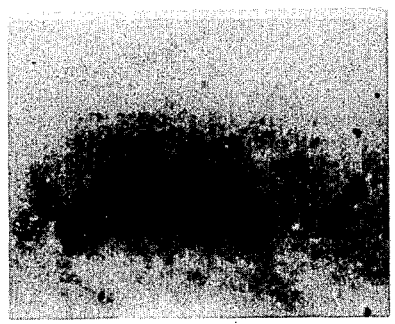

United States Patent [19]

Matsui

[11] 4,198,382

[45] Apr. 15, 1980

[54] NOVEL CARBON-CARBON COMPOSITE MATERIAL AND METHOD FOR ITS PRODUCTION

[75] Inventor: Hironori Matsui, Hirakata, Japan

[73] Assignee: Kanebo Ltd., Tokyo, Japan

[21] Appl. No.: 938,920

[22] Filed: Sep. 1, 1978

[30] Foreign Application Priority Data

Sep. 9, 1977 [JP] Japan .................................. 52/109078

[51] Int. Cl.$^2$ ............................................ C01B 31/02
[52] U.S. Cl. ...................................... 423/445; 106/56; 264/29.1; 423/449
[58] Field of Search .................... 423/445, 449, 447.1, 423/447.2; 264/29.1, 29.2; 106/56

[56] References Cited

U.S. PATENT DOCUMENTS

| | | | |
|---|---|---|---|
| 3,109,712 | 11/1963 | Bedfern ................................ | 423/449 |
| 3,814,642 | 6/1974 | Araki et al. ........................... | 156/60 |
| 4,039,341 | 8/1977 | Cooper et al. ..................... | 423/445 X |

FOREIGN PATENT DOCUMENTS 49-27513  7/1974  Japan ..................................... 264/29.1

OTHER PUBLICATIONS

Bradshaw et al., "11th Biennial Conference on Carbon Extended Abstracts & Program", Jun. 1973, pp. 271-272.

Jenkins et al., Proc. R. Soc. Lond. A 327 (1972), pp. 501-517.

*Primary Examiner*—Edward J. Meros
*Attorney, Agent, or Firm*—Wenderoth, Lind & Ponack

[57] ABSTRACT

The present invention provides a carbon-carbon composite material consisting of a matrix carbon and a fibrous reinforcing carbon, said matrix carbon consisting substantially of optically anisotropic carbon and said fibrous reinforcing carbon consisting substantially of optically isotropic carbon, and said matrix carbon and fibrous reinforcing carbon forming an interface without an intervening third material, wherein said composite material has a fracture surface showing a uniform vitreous light reflection, and a method for the preparation thereof. The composite material has a high flexural strength and a very low gas permeability and is useful as a molding material in the fields of high temperature chemistry, the atomic energy industry and medicine.

19 Claims, 6 Drawing Figures

2θ DEGREES

NOVEL CARBON-CARBON COMPOSITE MATERIAL AND METHOD FOR ITS PRODUCTION

This invention relates to a novel carbon-carbon composite material, more specifically to a vitreous carbon-carbon composite material composed of a substantially optically anisotropic carbon materix and a substantially optically isotropic fibrous reinforcing carbon and having a high flexural strength and a very low gas permeability, and to a method for its production.

Carbon fibers have a high tensile strength, and "carbon-carbon composite materials" have heretofore been produced by combining them with other carbonaceous materials.

The carbon-carbon composites have a very high flexural strength and tensible strength, and are free from the notion of brittle and weak materials which carbon material gives. They are expected to find extensive applications in the electronics industry, the atomic energy industry, the aerospace industry, etc. by taking advantage of their valuable properties such as high strength, thermal stability and abrasion resistance. Moreover, because the carbon-carbon composites have excellent affinity for the living body, they are also expected to be used in artificial bones and roots of teeth.

Some methods for producing these carbon-carbon composite materials have been suggested in the past.

One of them comprises simply shaping a tow, woven or knitted fabric or non-woven fabric of carbon fibers obtained by carbonizing cellulose or polyacrylonitrile fibers, placing the shaped product in a furnace, heating it to 1,000° to 1,500° C., introducing a hydrocarbon gas into the furnace to decompose and carbonize it at the surface of the carbon fibers, and thus to deposit carbon on the surface of the carbon fibers (this method will be referred to hereinbelow as the CVD method). [See, for example, Super-Temp. Corp. "RPG", Sante Fe Springs, California, U.S.A.]

The carbon-carbon composite material obtained by the CVD method, when having a fiber content of, say, 35% by volume, has a flexural strength of 9 to 15 kg/mm$^2$ which is 5 to 6 times that of synthetic graphite, but has the defect that its impact strength is as low as 2 to 4 kg.cm/cm$^2$. Furthermore, in the process of its production, the hydrocarbon gas must be heat-decomposed in such a manner as not to generate soot. The method, therefore, has low productivity, and a fairly high level of technique is required to produce uniform carbon material with a reduced number of pores.

Another method comprises shaping a tow, woven or knitted fabric, or non-woven fabric of carbon fibers obtained by carbonizing cellulose or polyacrylonitrile fibers by using a thermosetting resin, heat-treating the shaped product in an inert gas atmosphere to carbonize the resin, and if required, repeating the above steps after cooling (to be referred to as the RP method) [see Carborundum Graphite Products Division, "carbitex", Sanborn, New York, U.S.A.].

The carbon-carbon composite material obtained by the RP method, when having a fire content of 50% by volume, has an impact strength of 12 to 18 kg.cm/cm$^2$ which is far larger than the composite material obtained by the CVD method, but its flexural strength is 6 to 11 kg/mm$^2$ which is not as high as that of the CVD-method composite.

It has recently been reported in Japanese Patent Publication No. 27513/74 that a carbon-carbon composite material is made by shaping a fibrous product composed of natural or synthetic fibers together with a matrix such as a thermoplastic resin, a thermosetting resin, a mixture of such a resin and a filler, pitch and asphalt, and firing the shaped product. It is difficult, however, to produce by this method a completely unitary carbon-carbon composite of the matrix carbon and the fibrous reinforcing carbon. Production of a carbon-carbon composite having a high strength requires a special care and a long period of time. The method can neither give a composite having superior non-permeability as in vitreous carbon bodies.

U.S. Pat. No. 3,814,642 discloses a method for producing a carbon-carbon composite which comprises mixing an organic fiber produced by heat-treating a fiber such as pitch fibers, polyacrylonitrile fibers or polyvinyl alcohol fibers at a temperature of between normal temperature and 350° C. in an oxidizing gas atmosphere with an organic binding material, such as a phenol resin, furfural resin or coal tar, having a carbonization yield of more than 10%, said organic fiber being a precursor for carbon fibers and constituting a bulk material as well as a reinforcing material for the shaped carbon article, and having an average fiber diameter of less than 40 microns, a ratio between the fiber length and the diameter of more than 5, a hydrogen/carbon atomic ratio (H/C) of from 0.25 to 0.8 based on the elementary analysis, an ether-bonded type oxygen content of from 3 to 15%, a carbonization yield of from 50 to 92%, and a linear shrinkage of from 4 to 25% at a temperature of 1,000° C., pre-shaping the mixture, and firing the precursor. According to this method, however, the preliminary heat-treatment is carried out in oxidizing gas atmosphere and no special consideration is given to the bonding of the organic fibers to the matrix resin at their interfaces in the precursor. Hence, voids tend to form in the carbonized organic fiber portion, and the bonding of the fibers to the matrix in the precursor is not sufficient. Moreover, it cannot withstand various stresses generated within the precursor during firing (e.g., shrinkage, tension, gas evolution) and scale-like swellings called "blisters" or cracks occur. Naturally, the yield of the final product is extremely poor. For the same reason, the method of this patent gives only such a carbon-carbon composite product in which the fibrous carbon and the matrix carbon are bonded loosely to provide a discernible interface and cannot afford a composite having a sufficiently high gas permeability.

Furthermore, in the method of above U.S. Pat. No. No. 3,814,642, if the firing temperature is increased in order to use the composite material for applications requiring a high purity, for example as a crucible for semiconductors, the resulting carbon-carbon composite is more susceptible to graphatization than ordinary vitreous carbon bodies, and its gas-impermeability decreases. At the same time, its chemical resistance and resistance to air oxidation are deteriorated, thus presenting the outstanding differences in properties which have been well known to exist between graphatized products and vitreous carbon products.

When the cross sections of these carbon-carbon composites suggested heretofore are examined with unaided eyes or an ordinary reflective microscope, a boundary between the fibrous reinforcing material and the matrix is clearly observed. This fact indicates that a third material, for example air, is present between the reinforcing material and the matrix, and the closeness of the properties of the two carbon materials or the integration of these materials is not complete. This is considered to be the reason why these composites cannot have a high degree of non-permeability.

One object of this invention is to provide a novel and improved carbon-carbon composite which is free from the defects described hereinabove.

Another object of this invention is to provide a vitreous carbon-carbon composite which consists of a substantially optically anisotropic carbon matrix and a substantially optically isotropic fibrous reinforcing carbon and has a very high flexural strength and a very low gas permeability.

Still another object of this invention is to provide a method for producing such a novel carbon-carbon composite material with commercial advantage.

Other objects and advantages of this invention will become apparent from the following description.

According to this invention, there is provided a carbon-carbon composite material consisting of matrix carbon and fibrous reinforcing carbon, said matrix carbon consisting substantially of optically anisotropic carbon and said fibrous reinforcing carbon consisting substantially of optically isotropic carbon, and said matrix carbon and fibrous reinforcing carbon forming an interface without an intervening third material, wherein said composite material has a fracture surface showing a uniform vitreous light reflection.

Figure 1B:
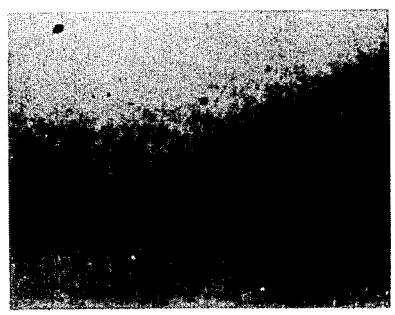
Figure 2:
Figure 2:
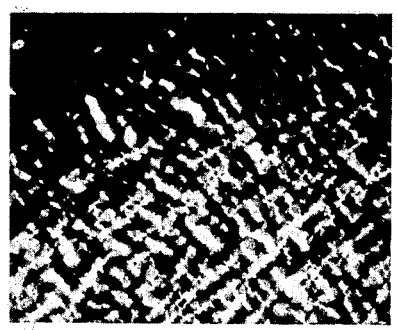
Figure 4:
Figure 3:
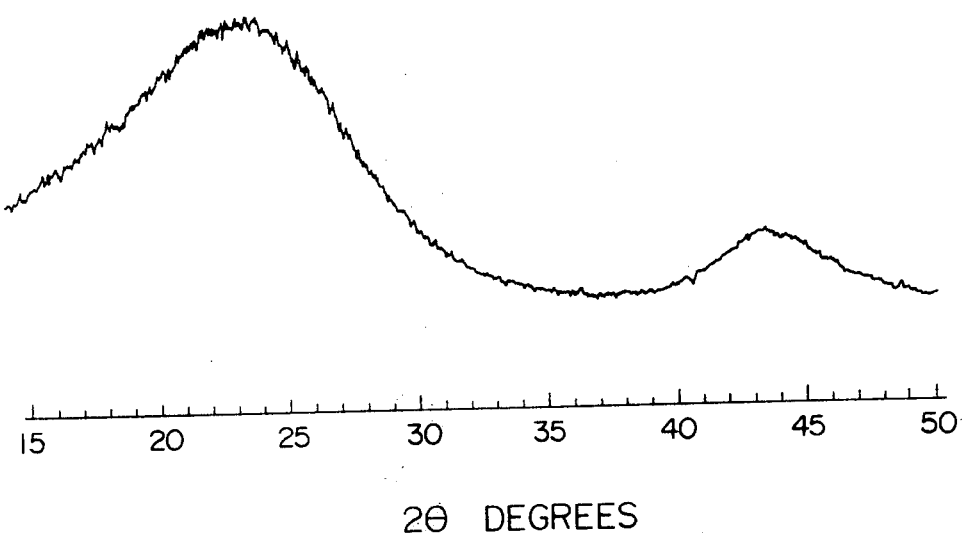

The carbon-carbon composite material of this invention will be described in more detail below taken partly in conjunction with the accompanying drawings in which:

FIGS. 1-a and 1-b are microphotographs of the cross-sections of the carbon-carbon composite material of this invention taken through a reflective microscope;

FIGS. 2-a and 2-b are microphotographs of the cross-sections of the carbon-carbon composite of this invention taken through a reflective polarized microscope;

FIG. 3 shows an X-ray diffraction pattern of a carbon-carbon composite material of this invention fired at 1000° C.; and FIG. 4 is a photograph of the fracture surface of the carbon-carbon composite of this invention, from which it will be appreciated that the fracture surface has a vitreous luster.

The carbon-carbon composite material of this invention is a structure which appears to be a completely unitary body of uniform quality in which the fibrous reinforcing carbon is completely integrated with the matrix carbon. Specifically, the fibrous reinforcing carbon and the matrix carbon form an interface without an intervening layer of a third material. In other words, the fibrous reinforcing carbon is directly bonded to the matrix carbon to form a unitary structure, and it has such a high degree of integration that the boundary line between the fibrous reinforcing carbon and the matrix carbon cannot be discerned not only with unaided eyes but also by a reflective microscope, as shown in FIGS. 1-a and 1-b.

However, the carbon-carbon composite material of the invention is greatly characterized by the fact that the matrix carbon and the fibrous reinforcing carbon can be differentiated from each other in optical properties, and the matrix carbon consists substantially of optically anisotropic carbon and the fibrous reinforcing carbon consists substantially of optically isotropic carbon. This can be confirmed easily by observing the composite of the invention by a reflective polarized microscope. This is why the carbon product of this invention is determined to be a carbon-carbon composite, and it is this characteristic that distinguishes the product of the invention clearly from conventional glassy or vitreous carbon bodies.

FIG. 1-a shows a microphotograph of that cross section of a carbon-carbon composite material (obtained by regularly aligning fibrous reinforcing materials in one direction) which is parallel to the fiber axis of the composite, as taken through an ordinary reflective microscope. FIG. 2-a shows a microphotograph of the same cross section as taken through a reflective polarized microscope by crossed Nicols at a diagonal position. FIG. 1-b shows a microphotograph of that cross section of the above carbon-carbon composite which is perpendicular to the fiber axis, as taken through an ordinary reflective microscope. FIG. 2-b shows a microphotograph of the same cross section as above taken by a reflective polarized microscope by crossed Nicols at a diagonal position.

It is clearly seen from FIGS. 1-a and 1-b that because in the carbon-carbon composite material of the invention, the properties of the matrix carbon and the fibrous reinforcing carbon are very close to each other and a third material, for example air, is substantially absent between the matrix and the reinforcing material, by observation under natural light, the matrix carbon and the reinforcing carbon are completely integrated and cannot be distinguished from each other at all, and no formation of an interface by the reinforcing material-third material-matrix is noted.

However, the matrix carbon and the fibrous reinforcing carbon in the carbon-carbon composite material of the invention have different optical properties. Thus, when it is observed by a polarized microscope between crossed Nicols while rotating a stage having the composite placed on it, the reinforcing carbon portion is always seen black, but the matrix portion changes in brightness according to the rotation of the stage and the light disappears four times while the stage rotates through 360°. This phenomenon demonstrates that the reinforcing carbon is optically isotropic, and the matrix carbon is optically anisotropic.

In the carbon-carbon composite material of the invention, the integrity of the matrix carbon and the reinforcing carbon is so good as not to substantially permit the intervening of a third material between them. Despite this, the matrix carbon and the fibrous carbon do not form the same carbonized product, and the composite material still retains the structure inherent to carbon-carbon composite in which the fibrous carbon reinforces the matrix carbon. Because of this unique characteristic, the carbon-carbon composite material of the invention exhibits various superior physical properties such as low gas permeability and high flexural strength as will be described hereinbelow.

The matrix carbon and the fibrous reinforcing carbon which constitute the carbon-carbon composite of this invention may be composed of substantially amorphous carbon, and the carbon-carbon composite of this invention, as a whole, may consist substantially of amorphous carbon. When a powder of the carbon-carbon composite of this invention is measured by an X-ray diffraction method, it generally does not show a sharp diffraction profile at a diffraction angle of 26° [the diffraction angle at (002) plane] inherent to crystalline carbon, i.e. graphite, but shows a broad diffraction profile at a diffraction angle of 26°, as shown in FIG. 3. Furthermore, the X-ray diffraction pattern of graphite shows a separated diffraction profile at a diffraction angle of 42° [the diffraction angle at the plane (101)] and a diffraction angle of 44° [the diffraction angle at the (100) plane]. The carbon-carbon composite material of this invention generally does not show a separated diffraction profile at a diffraction angle of 42 to 46°.

Accordingly, the term "amorphous carbon", as used in the present specification and the appended claims, denotes carbon which shows a broad diffraction profile at a diffraction angle of 26° and does not show a clearly separated diffraction profile at a diffraction angle of 42° to 46°.

The fibrous reinforcing carbon can account for 30 to 90% by weight, preferably 50 to 80% by weight, of the weight of the carbon-carbon composite of this invention, and the remainder can consist of substantially amorphous but optically anisotropic matrix carbon.

The fibrous reinforcing carbon and the matrix carbon may have substantially the same density which is about 1.42 to 1.61 g/cm$^3$, preferably 1.48 to 1.58 g/cm$^3$. Thus, the carbon-carbon composite material of this invention may have a density of about 1.42 to 1.61 g/cm$^3$, preferably 1.48 to 1.58 g/cm$^3$.

Whether the fibrous reinforcing carbon and the matrix carbon have substantially the same density is determined from the fact that no boundary line can be found between them in a reflective microscopic examination of the cross section of the carbon-carbon composite and that the density of the composite does not substantially change with varying contents of the fibrous reinforcing carbon at the time of producing the carbon-carbon composite. This is because the carbon-carbon composite, once formed, cannot be separated into the fiber reinforcing carbon and the matrix carbon.

On the other hand, the carbon-carbon composite of this invention is of extremely high purity, and generally contains at least 94% by weight, preferably at least 96% by weight, and at times at least 98% by weight, of carbon.

One characteristic feature of the carbon-carbon composite of this invention is that in spite of the fact that it is composed of the fibrous reinforcing carbon and the matrix carbon, it has a fracture surface presenting a uniform vitreous light reflection same as in conventional carbon products called glassy carbon or vitreous carbon. Specifically, when a shaped article of the carbon-carbon composite of the invention is broken, the broken surface is very similar in appearance to that of a shaped article of glass. The broken surface appears uniform by observation with a reflective microscope and electron microscope and has a high level of luster, as shown in FIG. 4. Such a characteristic in appearance of the carbon-carbon composite of this invention is one of the important characteristics which enables it to be distinguished from conventional carbon-carbon composites.

Another characteristic of the carbon-carbon composite of this invention is that although the carbon-carbon composite is seen to be homogeneous in appearance, as described hereinbefore, when it is electrolytically etched as an anode in water acidified with sulfuric acid, a difference in the degree of etching arises between the matrix carbon and the fibrous reinforcing carbon.

When the composite of this invention used as an anode is electrolytically etched in an aqueous solution containing sulfuric acid in a concentration of 30 to 70% by weight, preferably about 50% by weight, at a current density of 100 to 1,000 mA/cm$^2$, preferably about 500 mA/cm$^2$, using lead or platinum as a cathode for at least 10 minutes, preferably for 20 to 60 minutes, the anode (i.e., the composite of this invention) is etched by the attack of nascent oxygen. A clear difference in the degree of etching is observed between the matrix carbon and the fibrous reinforcing carbon in the composite of the invention. Generally, the degree of etching is large in the matrix carbon, and is small at the fibrous reinforcing carbon. Hence, the electrolytically etched composite material of this invention presents such an appearance that the fibrous reinforcing carbon portion is raised and the matrix carbon portion is depressed.

By virtue of the aforesaid characteristics, the composite of this invention exhibits various superior mechanical, electrical, physical and chemical properties.

For example, the composite of this invention, depending upon its composition, has a flexural strength of at least 9 kg/mm$^2$, preferably at least 10.5 kg/mm$^2$, more preferably 11.5 to 14.0 kg/mm$^2$. Moreover, the composite of this invention is very compact, and has a very low gas permeability. For example, its permeability to a helium gas is generally not more than $10^{-6}$ cm$^2$/sec, preferably not more than $10^{-7}$ cm$^2$/sec, and more preferably not more than $10^{-8}$ cm$^2$/sec.

Thus, despite its high compactness, the composite of the invention has a high impact strength of usually at least 2.5 kg.cm/cm$^2$, preferably at least 3.5 kg.cm/cm$^2$, more preferably 4.0 to 10.0 kg.cm/cm$^2$.

The composite of the invention is very hard as demonstrated by its Vickers hardness of at least 350 kg/mm$^2$, preferably at least 800 kg/mm$^2$, more preferably at least 1,000 kg/mm$^2$.

The electric conductivity of the composite of this invention is lower than that of ordinary carbon products or graphite. Generally, it has a specific electrical resistance of $10-10^{-4}$ ohm-cm, preferably $10^{-1}-10^{-3}$ ohm-cm, more preferably $10^{-2}-10^{-3}$ ohm-cm. The thermal conductivity of the composite of the invention is far lower than those of ordinary carbon products or graphite, and may usually be 1 to 40 kcal/m.hr.°C., especially 2 to 10 kcal/m.hr.°C.

The composite of this invention also has superior thermal stability, and can sufficiently withstand temperatures of generally up to about 545° C., and usually up to about 510° C., in the air. It has very good chemical resistance, and is not attacked by most organic and inorganic chemicals and are found passable in chemical resistance tests in most chemicals.

The carbon-carbon composite of this invention is therefore useful as a material for a reaction apparatus involving the use of corrosive liquids or gases, a heat exchanger, a thermocouple-protecting tube, an electrode, etc. in the high temperature chemical industry; as a coating material for waste matter, for example, in the atomic energy industry; as a material for semiconductors; and as roots of teeth or artificial joints, etc. in the medical field.

According to this invention, the carbon-carbon composite having the aforesaid superior characteristics can be advantageously produced by a method which comprises heat-treating cured novolac fibers at a temperature of from 250° C. to less than 500° C. in a non-oxidizing atmosphere; shaping a resinous composition consisting of 30 to 90% by weight of the resulting heat-treated and cured novolac fibers and 10 to 70% by weight of a phenolic resin calculated as the solids content of the cured phenolic resin; curing the shaped product; heating the cured product in a non-oxidizing atmosphere in such a manner that at least within the range of 200° to 500° C., the heating is carried out at a rate of not more than 60° C. per hour; and firing the product at a temperature of at least 800° C.

A first characteristic of the method of this invention is that cured novolac fibers which become a source of the fibrous reinforcing carbon are heat-treated in a non-oxidizing atmosphere at a temperature of from 250° C. to less than 500° C. before mixing them with a phenolic resin binder which will be carbonized to matrix carbon.

The cured novolac fibers used as a starting material in this method can be produced by melt-spinning a novolac resin, and curing the resulting novolac fibers with an aldehyde.

The novolac resin is an uncured meltable thermoplastic resin which can be produced by reacting (polycondensing) a phenol and an aldehyde under heat, usually in the presence of an acidic catalyst. In the present invention, novolac resins having a number average molecular weight of usually about 500 to about 2,000, especially about 700 to about 1,500 are used.

The phenols used for producing the novolac resins are most commonly phenol and cresol. But other phenols can also be used. Examples of these phenols are phenol, o-cresol, m-cresol, p-cresol, 2,3-xylenol, 2,5-xylenol, 2,4-xylenol, 2,6-xylenol, 3,4-xylenol, 3,5-xylenol, o-ethylphenol, m-ethylphenol, p-ethylphenol, p-phenylphenol, p-tertiary butyl phenol, p-tertiary amylphenol, bisphenol A, resorcinol, and mixtures of two or more of these phenols.

The aldehyde most commonly used for polycondensing with the above phenols is formaldehyde, but monoaldehydes and dialdehydes such as paraformaldehyde, hexamethylenetetramine, furfural, glutaraldehyde, adipoaldehyde and glyoxal can also be utilized.

The acidic catalyst used for the reaction of forming the novolac resins may be any known organic or inorganic acid, for example, hydrochloric acid, nitric acid, sulfuric acid, phosphoric acid, formic acid, p-toluenesulfonic acid, acetic acid, oxalic acid or phthalic acid.

Methods for producing novolac resins from such phenols and aldehydes are well known in the art, and they can be produced, for example, by the method described in U.S. Pat. No. 3,650,102.

Melt-spinning of novolac resins has also been well known. Novolac fibers can be produced, for example, by the method described in the above-cited U.S. Pat. No. 3,650,102 which comprises heating a novolac resin in an atmosphere of an inert gas such as carbon dioxide or nitrogen to form a flowable melt, and extruding or drawing the melt into an inert cooling medium such as air, nitrogen or water through a spinneret having nozzles of the desired size to cool and solidify the filaments.

According to the method of this invention, the inclusion of at most 30% by weight, preferably at most 15% by weight, based on the weight of the novolac resin, of another fiber-forming thermoplastic resin such as polyamides, polyurethane, polyesters, or polyolefins is permissible during the melt-spinning of the novolac resin.

The uncured novolac fibers so spun are then cured. The curing can also be performed by a known method. For example, the novolac fibers are heated to a temperature of about 90° to 105° C. in an aqueous solution containing an acid catalyst and an aldehyde. Or the uncured novolac fibers are pre-cured by heating them to a temperature of about 70° to 105° C. in an aqueous solution containing an acidic catalyst and an aldehyde, and the pre-cured novolac fibers are then heated in an aqueous solution containing a basic catalyst and an aldehyde to a temperature of about 70° to 95° C. Examples of suitable aldehydes and acidic catalysts for use in the curing of the novolac fibers are those given hereinabove for the production of novolac resins. Examples of the basic catalyst are sodium hydroxide, potassium hydroxide, calcium hydroxide, barium hydroxide, lithium hydroxide, magnesium hydroxide, strontium hydroxide, ammonia, dimethylamine, methylamine, and hexamethylenetetramine. Usually, ammonia and hexamethylenetetramine are used advantageously.

The methylol group content of the cured novolac fibers so prepared is not critical, but the cured novolac fibers may conveniently have a methylol group content of at least 3.5% by weight, preferably 4 to 12% by weight, more preferably 5 to 10% by weight. It has been found that by using cured novolac fibers having such a specified methylol group content, even when the methylol group content decreases as a result of the subsequent heat-treatment of the cured novolac fibers, the methylol groups remaining on the surface of the heat-treated novolac fibers may react effectively with the phenolic resin as a matrix to form a compactly integrated carbon-carbon composite in which the fibrous reinforcing carbon and the matrix carbon form an interface without an intervening third material, and the yield of the carbon-carbon composite can be increased greatly.

Adjustment of the methylol group content of the cured novolac fibers to the aforesaid range can be achieved by properly controlling the concentrations of the acidic or basic catalyst and the aldehyde in the curing bath, and/or the reaction time. The suitable concentration of catalyst is 10 to 20% by weight, and the suitable concentration of the aldehyde is 6 to 18% by weight. The reaction time is preferably 3 to 15 hours.

The "methylol group content" of the cured novolac fibers, as used in the present specification and the appended claims, is determined by the method to be described hereinbelow.

The cured novolac fibers obtained are then heat-treated by the method of the invention. The heat-treatment can be performed usually under no tension by using an ordinary heating means such as an electric furnace or an infrared induction furnace at a temperature of 250° to less than 500° C., preferably from 270° to 440° C., more preferably from 280° to 350° C. The heat-treatment should be performed in an atmosphere of a non-oxidizing gas. The heat-treatment is an oxidizing gas atmosphere taught by the above-cited U.S. Pat. No. 3,814,642 cannot give carbon-carbon composites having the various superior characteristics described hereinabove. The term "non-oxidizing atmosphere", as used herein, denotes an atmosphere from which air has been substantially expelled by pressure reduction, or an atmosphere of an inert gas such as nitrogen gas, carbon dioxide gas, carbon monoxide gas, argon gas and helium gas.

In the heat-treatment of the cured novolac fibers, the rate of temperature elevation from room temperature to the heat-treating temperature is not critical. Generally, it is appropriate to elevate the temperature at a rate of 0.5° to 50° C. per minute, preferably 1.0° to 20° C. per minute.

The heat-treatment time depends upon the heat-treatment temperature. Generally, it may be short at higher temperatures, and a longer period of time is required at lower temperatures. Generally, the heat-treating time may be 5 to 180 minutes, preferably 15 to 120 minutes.

In order to obtain especially advantageous results, it has been found desirable to control the heat-treatment so that in the infrared absorption spectrum of the heat-treated novolac fibers, the ratio ($D_{770}/D_{1600}$) of the absorption wavelength intensity ($D_{770}$) of an absorption peak under 740 to 770 cm$^{-1}$ ascribable to adjacent hydrogen atom on the benzene ring to the absorption wavelength intensity ($D_{1600}$) of an absorption peak near 1600 cm$^{-1}$ ascribable to the benzene ring generally becomes 0.05 to 0.40, preferably 0.10 to 0.35, and more preferably 0.15 to 0.30.

The absorption wavelength intensity ratio ($D_{770}/D_{1600}$) is a measure of the degree of growth of the three-dimensional linkage of the novolac fibers after heat treatment. It is believed that by heat-treating the novolac fibers so that the ratio ($D_{770}/D_{1600}$) is within the range of 0.05 to 0.40, the matrix carbon shows optical anisotropy and the reinforcing carbon shows optical isotropy, and in conjunction with the effect of the remaining methylol groups, the matrix carbon and the reinforcing carbon form an interface without an intervening third material, and that because the fracture surface of the composite shows a uniform vitreous light reflection, the resulting carbon-carbon composite has superior characteristics such as high flexural strength and low gas permeability.

The mechanism by which such a very unique characteristic is exhibited will be further described below.

Investigations of the present inventors show that when a carbon-carbon composite is produced by the same method as the method of the invention using non-heat-treated cured novolac fibers (usually having a $D_{770}/D_{1600}$ ratio of about 0.5), the matrix carbon and the reinforcing carbon are both optically isotropic and are fully integrated. This is probably because the matrix and the reinforcing fiber have substantially the same shrinkage at the time of carbonization.

When a carbon-carbon composite is produced by the same method as the method of the invention using cured novolac fibers which have been heat-treated at a temperature of more than 500° C. so that the ($D_{770}/D_{1600}$) ratio becomes less than 0.05, the reinforcing fibrous carbon scarcely shrinks and stress occurs by the difference in shrinkage between it and the matrix. Thus, graphatization (stress graphatization) takes place very easily, and voids occur even in the matrix to increase the gas permeability of the final product.

When the cured novolac fibers are heat-treated at the temperatures specified above so that the ratio ($D_{770}/D_{1600}$) is within the above-specified range, some stress is built up in the matrix because the matrix and the reinforcing fiber begin to shrink at different temperatures (naturally, the matrix shrinks earlier). But at the time of firing at 800° C. or more, the matrix is not graphatized because the matrix and the reinforcing fibrous carbon have substantially the same shrinkage. Accordingly, the matrix will have optical anisotropy. As a result, the increasing of the degree of the three-dimensional linkage of the novolac fibers by heat-treatment (namely, the increased fiber strength) results synergistically with the effect of bonding the matrix to the reinforcing fibrous carbon by an activating group typified by a methylol group which remains in the heat-treated novolac fibers. This finally leads to a carbon-carbon composite having the superior characteristics described hereinabove.

Desirably, the novolac fibers so heat-treated have a fiber length of generally at least 0.4 mm, preferably at least 1.0 mm. The fiber diameter is not critical, but is advantageously in the range of usually 5 to 60 microns, preferably 10 to 40 microns. Thus, heat-treated novolac fibers that can be used suitably in the method of this invention may have a length/diameter ratio of at least 40, preferably at least 100.

The heat-treated novolac fibers can be used in the method of this invention in the form of short or long fibers which are processed into a sheet, woven fabric, knitted fabric, non-woven fabric, roving, chopped strand, or staple. It is especially preferred to use them in the form of a woven fabric, non-woven fabric or staple.

The phenolic resin to be used in combination with the heat-treated novolac fibers is a pre-condensate produced by reacting a phenol such as those exemplified hereinabove for the production of novolac resins with an aldehyde such as those exemplified hereinabove for the production of novolac resins in the presence of an acidic or basic catalyst such as those exemplified hereinabove in accordance with well known methods. Usually, the phenolic resin includes self-heat-curable resols having a molecular weight of up to about 600 and a large methylol group content and obtained by reaction in the presence of a basic catalyst, and thermoplastic novolacs having a molecular weight of 300 to 2,000 in which the phenol is bonded mainly through a methylene linkage and which are obtained by reacting the phenol with the aldehyde in the presence of an acidic catalyst. In the method of this invention, the resols can be used especially advantageously.

According to the method of this invention, the heat-treated novolac fibers and the phenolic resin are mixed to form a resinous composition having the heat-treated fibers dispersed in a matrix of the phenolic resin. Mixing of the heat-treated fibers with the phenolic resin can be performed by known methods. For example, when the phenolic resin is a liquid, it is impregnated into a structure composed of the fibers. When the phenolic resin is a solid, it is finely pulverized, and then kneaded with the fibers by using a kneader, hot rolls, etc.

The mixing ratio between the heat-treated fibers and the matrix of the phenolic resin can be varied over a wide range according, for example, to the form of the heat-treated novolac fibers, the methylol group content of the novolac fibers before the heat-treatment, the infrared absorption wavelength intensity ratio, and the type of the phenolic resin. The amount of the heat-treated fibers is generally 30 to 90% by weight, preferably 40 to 85% by weight, more preferably 50 to 80% by weight, based on the weight of the resinous composition. The phenolic resin, on the other hand, can be incorporated in an amount of 10 to 70% by weight, preferably 15 to 60% by weight, more preferably 20 to 50% by weight, calculated as the solids content of the cured phenolic resin based on the weight of the resinous composition.

In the present specification and the appended claims, the amount of the phenolic resin is shown in terms of the solids content of the cured phenolic resin. The amount of the phenolic resin to be actually mixed in a given process can be readily determined by curing the same phenolic resin by the same method as will be used in the process and calculating the ratio of the weight of the phenolic resin before curing to that of the cured phenolic resin; and multiplying the solids content of the cured phenolic resin by the calculated ratio.

If desired, the resinous composition may include other additives such as a furan-type resin, an epoxy-type resin, a mixture of a vinyl polymer and a divinyl compound, a urea resin, an unsaturated polyester resin, a melamine resin, and a pitch or petroleum resin in a small amount of, say, not more than 20% by weight based on the weight of the phenolic resin.

The resinous composition so prepared is then shaped into a desired form such as a sheet, rod, cylinder, block, film, sphere or capsule. It is important to produce the shaped article in a larger size than is actually required because the product will shrink in the subsequent heating and firing steps. The shaping operation can be performed by applying known FRP (fiber-reinforced plastic) shaping methods such as a mold method, a hand lay up method, a spray up method, a filament winding method, a centrifugal molding method, a plutrusion method, a prepreg mat method, a premix method, a preform method, and a cross winding method. Of these, the methods involving molding under pressure are preferred.

The resinous composition so shaped can be cured as such or under a pressure of preferably about 10 to 300 kg/cm².

Curing of the shaped resinous composition can be performed in accordance with an ordinary curing method for phenolic resins, usually by heating. When the matrix phenolic resin is a resol resin, the composition is simply heated at a temperature of usually 110° to 180° C., preferably 130° to 160° C., for about 0.15 to 24 hours without using a curing agent. When the matrix phenolic resin is a novolac resin, at least 1 equivalent, preferably 1.1 to 2.0 equivalents, per equivalent of the novolac resin, of formaldehyde or a compound capable of releasing formaldehyde under the curing conditions such as hexamethylene tetramine, paraformaldehyde, trioxane, tetraoxane or glyoxal is introduced at the time of combining the heat-treated novolac fibers or a fibrous structure composed of the fibers with the novolac resin, and in the presence of such a curing agent, the shaped resinous composition is heated at a temperature of 110° to 180° C., preferably 130° to 160° C., for 0.15 to 24 hours.

The shaped and cured resinous composition is then heated to a carbonization temperature of at least 800° C., preferably at least 1,000° C., most suitably at least 1,200° C., in a non-oxidizing atmosphere, that is, under reduced pressure or in an atmosphere of an inert gas such as nitrogen gas, carbon dioxide gas, carbon monoxide gas, argon gas, and helium gas. There is no upper limit to the firing temperature, but from the standpoint of equipment and economy, temperatures of up to 3,500° C. are sufficient.

Another great characteristic of the method of this invention is that in the heating step, at least within the range of 200° to 500° C., the heating is carried out at a rate of not more than 60° C./hour, preferably not more than 40° C./hour, more preferably not more than 20° C./hour. Within the temperature ranges lower than 200° C. and higher than 500° C., the heating may be carried out at the above specified rates or at faster rates.

The present inventor has found that at about 200° C., gaseous oxygen compounds such as $H_2O$, HCHO, CO and $CO_2$ begin to be released from the shaped resinous composition, and at temperatures above 500° C., evolution of hydrogen gas is observed.

It has been found specifically that within a range of 200° to 500° C., the methylol groups remaining in the heat-treated novolac fibers may chemically react in various ways with reactive residues (e.g., a methylol group) in the matrix of cured phenolic resin to absorb the generated distortions and integrate the resinous composition, and the integrated composition is then submitted to a carbonization treatment at high temperatures. Accordingly, special care must be taken about the rate of temperature raise within this temperature range, and it has been found that the rate of heating is very desirably not more than 60° C./hour. When the rate of heating is faster than 60° C./hour, the resinous composition is carbonized without the absorption of the distortions and slow chemical reactions. Accordingly, the resulting carbon-carbon composite will be unacceptable because of blisters or cracks formed or of poor strength, and the yield of the product will decrease.

The heating of the shaped and cured resinous composition can be performed in a customary manner by maintaining it in a single furnace, a continuous furnace, an electric firing furnace or a tunnel furnace at the aforesaid firing temperature for at least about 0.15 hour, usually 1 to 72 hours.

The carbonized carbon-carbon composite is cooled to below about 500° C., and then withdrawn from the furnace.

The method of this invention described hereinabove can afford a carbon-carbon composite having the aforesaid characteristics.

According to the method of this invention, carbon-carbon composites of various shapes and sizes can be freely and easily produced, and the yield of the product in commercial production is good. The firing time can be drastically shortened, and the cost of production can be reduced.

The following Examples further illustrate the present invention.

The various properties indicated in the following Examples were measured by the following methods.

(1) Determination of methylol groups in the cured novolac fibers

Preparation of a calibration curve

A novolac resin being substantially free from a methylol group (i.e., no absorption at 995 cm$^{-1}$ ascribable to the methylol group in the infrared absorption spectrum determined by the KBr tablet method) and having a number average molecular weight of 1,000 (intrinsic viscosity $[\eta]$ of 0.076) was mixed uniformly with a resol having a known methylol group content. The infrared absorption spectrum of the mixture was determined by the KBr tablet method. By an analytical method to divide the overlapping peak of the spectrum, the absorption intensity (to be referred to as "$D_{995}$") at 995 cm$^{-1}$ (an absorption peak ascribable to the methylol group) and the absorption intensity (to be referred to as "$D_{1600}$") at 1600 cm$^{-1}$ (an absorption peak ascribable to benzene) were determined, and the absorption intensity ratio ($D_{995}/D_{1600}$) was calculated.

The above procedure was repeated except the amount of the resol (i.e., the methylol group content) was varied.

The absorption intensity ratios and the total amount of the methylol groups in the resol mixture were plotted in a graph to form a calibration curve.

Determination of the methylol groups in the cured novolac fibers

A sample of the cured novolac fibers was pulverized in a mortar, and its infrared absorption spectrum was determined by the KBr tablet method. The absorption intensity ($D_{995}/D_{1600}$) was determined in the manner described above. The absorption intensity ratio was applied to the calibration curve previously prepared, and the methylol group content corresponding to the absorption intensity ratio was read. The value read was the methylol group content of the sample.

(2) Infrared absorption wavelength intensity ratio ($D_{770}/D_{1600}$) of the heat-treated novolac fibers A sample of heat-treated novolac fibers is pulverized in a mortar, and its infrared absorption spectrum by a KBr tablet method is taken. By an analytical method to divide an overlapping peak, the absorption wavelength intensity ($D_{770}$) of an absorption peak near 740–770 cm$^{-1}$ ascribable to adjacent hydrogen atoms on the benzene ring and the absorption wavelength intensity ($D_{1600}$) of an absorption peak near 1600 cm$^{-1}$ ascribable to the benzene ring are determined from the spectrum. The absorption intensity ratio ($D_{770}/D_{1600}$) is then calculated.

(3) Yield in the firing step

The number of perfectly finished carbon-carbon composites obtained was expressed in percent based on the number (100) of precursors charged into a firing furnace.

(4) Optical properties of the carbon-carbon composite

The cross-section of a carbon-carbon composite sample is observed by a reflective polarized microscope.

(5) Flexural strength of the carbon-carbon composite

Measured by a modified version of the method of JIS K6911.

(6) Impact strength of the carbon-carbon composite

The total impact energy which is absorbed when a test piece is broken is determined by a Charpy impact tester. The impact strength is obtained by dividing the total impact energy by the cross-sectional area of the notched portion of the test piece.

(7) Gas-permeability of the carbon-carbon composite

Measured by a volume changing method using a helium gas in a device substantially conforming to ASTM D-1434. In Examples 1 to 5, the logarithms of the gas permeabilities (cm$^2$/sec.) are described.

(8) Density

A sample was pulverized, and its density was measured by a floating-sinking method.

(9) Thermal stability of the carbon-carbon composite

Measured at a temperature at which a decrease in weight begins in a T.G.A. device in which the temperature was raised at a rate of 5° C./min. in the air.

(10) Hardness of the carbon-carbon composite

Measured by a Vickers method micro hardness tester under a load of 500 kg.

(11) X-ray diffraction pattern of the carbon-carbon composite

A sample was pulverized by a disc-type pulverizer made of tungsten carbide, and the X-ray pattern was measured by a diffractometer under the radiation of CuKα using a nickel filter.

(12) Specific electric resistance of the carbon-carbon composite

Measured by a voltage dropping method in accordance with JIS R-7202.

All percentages in the Examples are by weight unless otherwise indicated.

EXAMPLE 1

A 10-liter separable flask was charged with 6.5 kg of phenol, 3.4 kg of 44% by weight formaldehyde and 20 g of oxalic acid, and with stirring, the temperature was raised from 20° C. to 100° C. over the course of 5 hours. The mixture was maintained at this temperature for 1 hour, and then heated under a reduced pressure of 20 mmHg to elevate the temperature to 180° C. over the course of 3 hours to remove water, the unreacted substances and low-boiling compounds. The resulting novolac resin had a number average molecular weight of 1000 and a melt-softening temperature of 125° C.

The novolac resin was melt-spun at 148° C. by a spinneret having 120 orifices with a diameter of 0.20 mm, and taken up at a rate of 700 m/min. to form uncured novolac filaments having a denier of 1.85, a tenacity of 0.25 kg/mm$^2$ and an elongation of 16%. The filaments were then dipped in a mixed aqueous solution at 28° C. containing 17.5% by weight of hydrochloric acid and 14.5% by weight of formaldehyde, and the temperature of the aqueous solution was raised gradually to 98° C. over the course of 2 hours. Then, the filaments were maintained at 98° C. for 2 hours to form cured novolac filaments having a degree of curing (a weight increase) of 10%. The cured novolac fibers had a methylol group content of 4.5%.

The cured novolac filaments under no tension were heated from room temperature to each of the temperatures shown in Table 1 at a rate of 150° C. per hour in a stream of nitrogen gas, and treated at each of the temperatures for 1.0 hour.

The tenacities and infrared absorption wavelength intensities ($D_{770}/D_{1600}$) of the resulting heat-treated novolac filaments were measured, and the results are shown in Table 1.

The heat-treated filaments were cut to a length of 6 mm, and subjected to a beater to improve their dispersibility. The cut filaments were mixed with a resol resin having a gellation time of 100 seconds at 140° C. by a kneader so that the fiber content was as shown in Table 1. Each of the resinous compositions so obtained was dried indoors, then in an oven and finally in vacuum, and then weighed. Then, it was formed into a rectangular material for molding. The material was molded in a mold heated at 150° C., and cured to form a precursor having a width of 20 mm, a thickness of 20 mm and a length of 120 mm.

The precursor was heated in a stream of argon gas from room temperature to 200° C. at a rate of 100°

C./hour, and from 200° C. to 500° C. at a rate of 20° C./hour; and from 500° C. to 1000° C. at a rate of 80° C./hour, and further firing at 1000° C. for 5 hours.

The optical properties, gas permeabilities, flexural strengths, impact strengths and densities of the resulting carbon-carbon composites were measured, and the cross sectional surfaces of the specimens were observed by a reflective microscope.

The results are shown in Table 1.

the reinforcing carbon cannot be distinguished from each other by observation through a reflective microscope. It is believed from this that the densities of the matrix portion and the reinforcing portion have substantially the same density.

It has been found that carbon-carbon composites in Runs Nos. 3, 5 to 8 and 10 to 12 which are within the scope of the invention have a carbon content of 97 to 98% by weight, X-ray diffraction analysis showed that

Table 1

| Run No. | Heat-treating temperature for the cured novolac fibers (°C.) | Tenacity of the heat-treated fibers (g/d) | Infrared absorption wavelength intensity ratio ($D_{770}/D_{1600}$) of the heat-treated fibers | Content of the heat-treated fibers in the resinous composition (%) |
|---|---|---|---|---|
| 1 (comparison) | — | 1.74 | 0.52 | 50 |
| 2 (comparison) | 200 | 1.81 | 0.43 | 50 |
| 3 (invention) | 250 | 2.00 | 0.40 | 50 |
| 4 (invention) | 300 | 2.09 | 0.31 | 20 |
| 5 (invention) | 300 | 2.09 | 0.31 | 30 |
| 6 (invention) | 300 | 2.09 | 0.31 | 50 |
| 7 (invention) | 300 | 2.09 | 0.31 | 80 |
| 8 (invention) | 300 | 2.09 | 0.31 | 90 |
| 9 (comparison) | 300 | 2.09 | 0.31 | 95 |
| 10 (invention) | 350 | 2.23 | 0.28 | 50 |
| 11 (invention) | 400 | 2.58 | 0.20 | 50 |
| 12 (invention) | 440 | 2.65 | 0.11 | 50 |
| 13 (comparison) | 500 | 2.87 | 0.03 | 50 |
| 14 (comparison)* | 500 | 2.87 | 0.03 | 50 |

| Run No. | Differentiation between the matrix and the reinforcing material by a reflective microscope | Optical properties of the composite — Matrix | Optical properties of the composite — Reinforcing material | Logarithm of gas permeability | Flexural strength (kg/mm$^2$) | Impact strength (Kg·cm/cm$^2$) | Density (g/cm$^3$) |
|---|---|---|---|---|---|---|---|
| 1 (comparison) | No | Isotropic | Isotropic | −10 | 8.2 | 2.0 | 1.57 ± 0.05 |
| 2 (comparison) | No | Isotropic | Isotropic | −10 | 8.8 | 2.2 | 1.57 ± 0.05 |
| 3 (invention) | No | Anisotropic | Isotropic | −10 | 11.5 | 3.5 | 1.57 ± 0.05 |
| 4 (comparison) | No | Anisotropic | Isotropic | −10 | 8.3 | 2.3 | 1.57 ± 0.05 |
| 5 (invention) | No | Anisotropic | Isotropic | −10 | 12.7 | 3.0 | 1.57 ± 0.05 |
| 6 (invention) | No | Anisotropic | Isotropic | −10 | 13.2 | 4.7 | 1.57 ± 0.05 |
| 7 (invention) | No | Anisotropic | Isotropic | −10 | 11.9 | 6.6 | 1.57 ± 0.05 |
| 8 (invention) | No | Anisotropic | Isotropic | −7 | 9.6 | 7.0 | 1.57 ± 0.05 |
| 9 (comparison) | Formation of a precursor was difficult, and an analysis sample could not be obtained | | | | | | |
| 10 (invention) | No | Anisotropic | Isotropic | −9 | 13.0 | 5.7 | 1.57 ± 0.05 |
| 11 (invention) | No | Anisotropic | Isotropic | −8 | 11.8 | 7.2 | 1.57 ± 0.05 |
| 12 (invention) | No | Anisotropic | Isotropic | −7 | 10.3 | 8.0 | 1.57 ± 0.05 |
| 13 (comparison) | Yes | Anisotropic | Isotropic | >−1 | 6.9 | 11.2 | <1.35 |
| 14 (comparison)* | Yes | Anisotropic | Isotropic | −3 | 12.4 | 13.4 | 1.53 ± 0.05 |

*The resol resin was again impregnated into the sample of Run No. 13, cured and then re-fired. This cycle was repeated four times.

The following conclusion can be drawn from Table 1.

When cured novolac fibers treated at a temperature lower than 250° C. are used, the resulting product is a glassy carbon body rather than a carbon-carbon composite. Although this product has superior gas-impermeability, its flexural strength and impact strength are not entirely satisfactory. When cured novolac fibers heat-treated at 500° C. or higher are used, the matrix and the reinforcing carbon in the resulting composite can be distinguished even with unaided eyes, and the product has poor gas-impermeability.

When the content of the heat-treated novolac fibers in the resinous composition is less than 30%, the purpose of reinforcing cannot be achieved, and the strength of the product is low. If the content exceeds 90%, it is difficult to mold a precursor itself, and a compact precursor cannot be obtained.

From Runs Nos. 5 to 8, no correlation is seen between the fiber content and the density of the resulting carbon-carbon composite, and the matrix carbon and they have a broad diffraction profile at a diffraction angle of 26° and do not show a profile separated into two peaks at a diffraction angle of 42° to 46°, and therefore that these composites consist as a whole an amorphous carbon.

EXAMPLE 2

The same novolac resin as used in Example 1 were spun under the same conditions as in Example 1. The resulting uncured novolac filaments were dipped in an aqueous solution of hydrochloric acid and formaldehyde in the various proportions shown in Table 2 with the ratio of the filaments to the aqueous solution being maintained at 1:20, and heated to 97° C. over the course of 3 hours, and maintained at 96° to 98° C. for 7 to 20 hours. The treated filaments were washed with water, dipped in an aqueous solution containing 1% of ammonia and 55% of methanol and treated at 60° C. for 60 minutes, washed with water, and dried. The methylol group content of the resulting filaments was determined.

The resulting cured novolac filaments were heated under no tension in a stream of nitrogen gas from room temperature to 350° C. at a rate of 150° C. per hour, and maintained at this temperature for 1 hour. The tenacities of the resulting filaments were also measured.

Various carbon-carbon composites having a fiber content of 53% by weight were prepared from these heat-treated novolac fibers in the same way as in Example 1.

After firing, composites which developed blisters or cracks were removed, and the yields, optical properties, gas-impermeabilities, flexural strengths and impact strengths of the resulting carbon-carbon composites were measured.

The results are shown in Table 2.

Table 2

| | Curing bath | | Properties of cured novolac filaments | |
| --- | --- | --- | --- | --- |
| | Concentration | Concentration | Methylol group | Tenacity of the heat-treated |
| Run No. | of HCl (%) | HCHO (%) | content (%) | filaments (g/d) |
| 1 | 21.0 | 14.0 | 3 | 2.17 |
| 2 | 19.0 | 14.0 | 4 | 2.16 |
| 3 | 17.5 | 14.0 | 6 | 2.29 |
| 4 | 19.0 | 17.5 | 8 | 2.10 |
| 5 | 14.0 | 17.5 | 10 | 1.72 |
| 6 | 10.0 | 17.5 | 12 | 1.51 |

| | | Properties of carbon-carbon composite | | | |
| --- | --- | --- | --- | --- | --- |
| | | Optical properties | | Logarithm of gas | Flexural | Impact |
| Run No. | Yield (%) | Matrix carbon | Reinforcing carbon | perme-ability | strength (kg/mm$^2$) | strength (kg·cm/cm$^2$) |
| 1 | 68 | Anisotropic | Istropic | −6 | 11.3 | 5.9 |
| 2 | 85 | " | " | −8 | 12.9 | 5.6 |
| 3 | 96 | " | " | −10 | 13.5 | 5.2 |
| 4 | 100 | " | " | −10 | 13.8 | 4.7 |
| 5 | 99 | " | " | −10 | 13.2 | 3.8 |
| 6 | 87 | " | " | −10 | 12.0 | 2.7 |

The fracture surfaces of these carbon-carbon composites had a uniform vitreous light reflection, and when these fracture surfaces were observed by a reflective microscope, the matrix carbon and the fibrous reinforcing carbon could not be distinguished from each other because they were integrated to a very high degree.

These carbon-carbon composites had a carbon content of 97 to 98%, and X-ray analysis of these composites showed that they consisted as a whole of amorphous carbon.

EXAMPLE 3

Cured novolac filaments obtained in the same way as in Example 1 were heated under no tension in a stream of nitrogen gas from room temperature to 300° C. at a rate of 100° C. per hour, and maintained at 300° C. for 1.5 hours to form filaments having an infrared absorption wavelength intensity ratio ($D_{770}/D_{1600}$) of 0.26.

The resulting heat-treated filaments were cut to a length of 6 mm, and blended by a hot roller with a molding novolac resin (granule) having a number average molecular weight of 540 and containing 3% of hexamethylene tetramine so that the mixture contained 55% of the heat-treated fibers. Using the resulting resinous composition, a precursor was produced in the same way as in Example 1.

The precursor was heated in a stream of nitrogen gas from room temperature to 200° C. at a rate of 70° C. per hour, from 200° C. to 500° C. at each of the rates shown in Table 3, and from 500° C. to 1200° C. at a rate of 100° C. per hour, and fired at 1200° C. for 1 hour.

The yields, gas-permeabilities, flexural strengths and carbon contents of these carbon-carbon composites were measured, and the results are shown in Table 3.

Table 3

| Run No. | 1 | 2 | 3 (comparison) |
| --- | --- | --- | --- |
| Temperature elevating rates in the 200–500° C. range (°C. hr) | 20 | 60 | 100 |
| Yield (%) | 100 | 97 | 62 |
| Logarithm of gas-permeability | −10 | −8 | −7 |
| Flexural strength (kg/mm$^2$) | 13.4 | 12.7 | 5.8 |
| Carbon content (%) | 98.3 | 98.1 | 98.1 |

The cross-sections of the three carbon-carbon composites obtained had a uniform vitreous light-reflection. Observation of the cross-sections by a reflective microscope showed that in the product of Run No. 3, cracks formed between the matrix carbon and the reinforcing carbon and in the matrix carbon, but no such phenomenon was seen in the other two products of Runs Nos. 1 and 2. The optical properties of the products of Runs Nos. 1 and 2 were examined by a reflective polarized microscope. It was found that the matrix carbon was optically anisotropic, and the reinforcing carbon was optically isotropic. X-ray diffraction analysis of the two composites of Runs Nos. 1 and 2 showed that they consisted substantially of amorphous carbon.

EXAMPLE 4

The heat-treated novolac filaments obtained in Example 3 was dipped in a methanol solution of the same resol resin as used in Example 1, withdrawn, and dried to remove the methanol. Thus, a tow of the heat-treated novolac filaments surface-coated with the resol resin was obtained. The tow was cut to a length of 80 mm, and filled in a mold having a length of 80 mm, a thickness of 4 mm and a width of 10 mm while aligning the fiber axes in the longitudinal direction, followed by pressing at 150° C. to form a precursor having a fiber content of 48.5%.

The precursor was heated in the same atmosphere as used in Example 1 to each of the firing temperatures shown in Table 4 at the same temperature elevating rate as in Example 1, and maintained at each of the firing temperatures for 3 hours. Thus, five carbon-carbon composites were produced.

The gas-permeabilities, specific electric resistances, flexural strengths, thermal stabilities, and elemental analysis values of these composites were determined, and the results are shown in Table 4.

Resin N-2 was heated to 180° C. to form a novolac resin (N-3).

Resin N-3 was maintained at 180° C. for 1 hour to form a novolac resin (N-4).

Resin N-4 was defoamed at 180° C. under a pressure of 50 mmHg for 3 hours to form a novolac resin (N-5).

Resin N-5 was defoamed at 10 mmHg for 3 hours to form a novolac resin (N-6).

Resin N-6 was defoamed at 5 mmHg for 3 hours to form a novolac resin (N-7).

Resin N-6 was defoamed at 5 mmHg for 20 hours to form a novolac resin (N-8).

Resin N-8 was defoamed at 190° C. and $10^{-1}$ mmHg to form a novolac resin (N-9).

Table 4

| Run No. | Firing temperature (°C.) | Logarithm of gas permeability | Specific electric resistance (ohms · cm) | Flexural strength (kg/mm$^2$) | Thermal stability (°C.) | Elemental analysis values (%) | |
|---|---|---|---|---|---|---|---|
| | | | | | | Carbon | Hydrogen |
| 1 | 700 | −9 | $8 \times 10^4$ | 3.0 | 503 | 93.3 | 0.72 |
| 2 | 800 | −10 | $6 \times 10^0$ | 9.7 | 515 | 96.4 | 0.33 |
| 3 | 1000 | −10 | $1 \times 10^{-2}$ | 13.1 | 519 | 98.1 | 0.23 |
| 4 | 1200 | −10 | $8 \times 10^{-3}$ | 13.4 | 520 | 98.8 | 0.10 |
| 5 | 1800 | −9 | $1 \times 10^{-3}$ | 11.2 | 520 | 99.0 | 0.07 |

Those cross-sections of each of the carbon-carbon composites of the invention (Runs Nos. 2 to 5) which were parallel and perpendicular respectively to the fiber axis were observed by a reflective microscope. As a result, the matrix carbon and the reinforcing carbon could not be distinguished from each other, and no interface between the two carbons was seen. Further, these two cross-sections were observed by a reflective polarized microscope to determine the optical properties of each of these carbon-carbon composites. This led to the confirmation that the matrix carbon was optically anisotropic, and the reinforcing carbon was optically isotropic.

By X-ray diffraction analysis, these four carbon-carbon composites (Runs Nos. 2 to 5) were found to show a broad diffraction profile at a diffraction angle of 26°, and at a diffraction angle of 42° to 46°, the diffraction profile did not separate into peaks. From this result, these four carbon-carbon composites were found to consist substantially of amorphous carbon. The X-ray diffraction pattern of the carbon-carbon composite of Run No. 3 is shown in FIG. 3. The microphotographs of those cross-sections of the carbon-carbon composite of Run No. 2 which were parallel and perpendicular respectively to the fiber axis are shown in FIGS. 1-a, 1-b, 2-a and 2-b. FIGS. 1-a and 2-a show microphotographs of the cross sections parallel to the fiber axis, and FIGS. 1-b and 2-b show microphotographs of the cross-sections perpendicular to the fiber axis. FIGS. 1-a and 1-b were taken through a reflective polarized microscope using crossed Nicols a a diagonal position.

The properties of these carbon-carbon composite will be fully understood from these microphotographs.

EXAMPLE 5

A mixture of 113 g (1.20 moles) of phenol, 30 g (1.00 mole) of formaldehyde and 1 g of oxalic acid was heated from room temperature to 100° C. at a rate of 30° C./hour. The resulting novolac resin is referred to as resin N-1.

Resin N-1 was maintained at 100° C. for 1 hour to obtain a novolac resin (N-2).

The number average molecular weights of these novolac resins were measured, and the results are shown in Table 5.

Each of these novolac resins was melt-spun under optimal spinning conditions for each at an extruding pressure of 50 cm H$_2$O using a spinneret with an orifice diameter of 0.20 mm to form uncured novolac fibers. The maximum wind-up speed (m/min.) and the number of filament breakage during a period of 10 minutes at the same windup speed were measured. The results are shown in Table 5.

The uncured novolac fibers were cured at 97° C. for 7 hours in an aqueous solution containing 17.5% of hydrochloric acid and 14.0% of formaldehyde to form cured novolac fibers. The strengths of these fibers were measured, and are shown in Table 5.

The cured novolac fibers prepared from the novolac resins Nos. 1 to 9 were found to have a methylol group content of 6 to 7% by weight.

Table 5

| Novolac resin | Number average molecular weight of the novolac resin | Number of filament breakage during 10 minutes | Maximum wind-up speed (m/min.) | Strength of the cured novolac fibers (g/d) |
|---|---|---|---|---|
| N-1 | 320 | 8 | 240 | 0.9 |
| N-2 | 480 | 6 | 430 | 1.1 |
| N-3 | 540 | 0-2 | 820 | 1.5 |
| N-4 | 780 | 0-1 | 1000 | 1.7 |
| N-5 | 880 | 0-1 | 1200 | 1.8 |
| N-6 | 1000 | 0-1 | 1200 | 1.8 |
| N-7 | 1480 | 0-1 | 1200 | 1.7 |
| N-8 | 1880 | 0-2 | 800 | 1.5 |
| N-9 | 2210 | 6 | 410 | 0.9 |

Resins Nos. 3 to 8 had good spinnability, and the cured novolac fibers prepared from resins Nos. 4 to 7 had feasible strength.

These cured novolac fibers were heated under no tension in a stream of nitrogen gas from room temperature to 300° C. at a rate of 150° C. per hour, and maintained at this temperature for 1.0 hour. The nine heat-treated novolac fibers obtained had an infrared absorption wavelength intensity ratio ($D_{770}/D_{1600}$) in the range of 0.30 to 0.32.

The heat-treated novolac fibers were cut to a length of 10 mm, and formed into a precursor containing 50% by weight of the fibers and then fired in the same way as in Example 1.

The yields, flexural strengths and gas permeabilities of the resulting carbon-carbon composites were measured, and the results are shown in Table 6.

Table 6

| Novolac resin | Yield (%) | Flexural strength ($kg/mm^2$) | Logarithm of gas permeability |
| --- | --- | --- | --- |
| N-1 | 38 | 7.2 | −4 |
| N-2 | 57 | 9.1 | −6 |
| N-3 | 81 | 10.8 | −8 |
| N-4 | 94 | 12.4 | −9 |
| N-5 | 100 | 13.2 | −10 |
| N-6 | 100 | 13.4 | −10 |
| N-7 | 95 | 12.1 | −8 |
| N-8 | 81 | 9.3 | −6 |
| N-9 | 53 | 7.6 | −5 |

When the fracture surfaces of the resulting carbon-carbon composites were observed by a reflective microscope, the matrix carbon and the reinforcing carbon could not be distinguished from each other. When the optical properties of these composites were determined, the matrix carbon was found to be optically anisotropic and the reinforcing carbon was found to be optically isotropic.

These carbon-carbon composites had a carbon content of 97 to 98%.

EXAMPLE 6

The heat-treated novolac fibers prepared in Example 5 from novolac resin N-6 were cut to a length of 70 mm and spun on a spinning frame to form yarns having a twist of 13.9 T/in. The yarns were woven to form a twill fabric having a basis weight of 300 g/m². The fabric had a tensile strength of 33 kg/25 mm in the warp direction and 26 kg/25 mm in the weft direction.

The woven fabric was dipped in a methanol solution of a resol resin having a gellation time of 130° C.×110 sec, and then dried to form a prepreg having a fiber content of 50%. Fifteen prepregs were laminated and consolidated by a laminating press heated at 150° C. to form a precursor.

The precursor was fired in the same way as in Example 1 to afford a carbon-carbon composite having a thickness of 2.8 mm, a flexural strength of 13.0 kg/mm², a gas permeability of $10^{-10}$ cm²/sec., a Vickers hardness of 1,100 kg/cm², and a carbon content of 98.0% by weight.

The fracture surface of the carbon-carbon composite, as shown in FIG. 4, showed a uniform vitreous light reflection.

As a result of measuring its optical properties, the matrix carbon was found to be optically anisotropic, and the reinforcing carbon was found to be optically isotropic.

The resulting carbon-carbon composite was used an an anode, and electrolytically etched in a 50% by weight aqueous solution of sulfuric acid at a current density of 500 mA/cm² for 0.7 hour. A platinum plate having a sufficiently larger size than the anode was used as a cathode.

The surface of the composite before the etching and the etched surface of the composite were observed by a scanning electron microscope. After the etching, the matrix portion can be distinguished from the fibrous reinforcing portion because the degree of etching of the matrix portion is larger than that of the fibrous reinforcing portion.

The weight of the composite before the etching and that after the etching were measured. The electrolytic etching resistance, expressed by (the weight after the etching/the weight before the etching)×100, of the composite was 87%.

For comparison, a mixture obtained by adding 1% by weight of aniline sulfate to furfuryl alcohol was coated by the multilayer coating method disclosed in Japanese Patent Publication No. 5153/64 (by which the coating-curing cycle was repeated to form a thick coating) to form precursor. The precursor was fired in the same way as above to form a vitreous carbon product having substantially the same shape as the carbon-carbon composite described above.

The resulting vitreous carbon product had a gas permeability of $10^{-9}$ cm²/sec., but a flexural strength of as low as 7 kg/mm².

When the resulting vitreous carbon product was electrolytically etched under the same conditions as described above, no local variation in the degree of etching was observed, and the product was uniformly etched.

The electrolytic etching resistance of the vitreous carbon product, measured by the same method as in the carbon-carbon composite described above, was found to be 69%.

COMPARATIVE EXAMPLE 1

This example shows that cured novolac fibers heat-treated in an oxidizing gaseous atmosphere are not suitable as the fibrous reinforcing carbon.

Cured novolac filaments obtained in the same way as in Example 1 were heated in an oxidizing atmosphere containing 3% by volume of nitrogen dioxide ($NO_2$) from room temperature to 250° C. at a temperature elevating rate of 1.5° C. per minute. The treated filaments were found to have a tenacity of as low as 0.93 g/d.

The treated filaments were cut to a length of 70 mm, and spun on a spinning frame. Spinning, however, was difficult because these fibers were very weak.

The filaments were cut to a length of 3 mm, and formed into a sheet by an ordinary wet sheet-forming method using a resol resin as a binder to afford a paper-like sheet having a basis weight of 100 g/m² (the resol resin content 10%). The paper-like sheet was then impregnated with a laminating resol resin having a gellation time of 140 seconds at 140° C. so that the fiber content of the prepreg became 60%, and then pressed to make it compact. Such compacted prepregs were laminated, and consolidated at 150° C. and 30 kg/cm² for 30 minutes to form a laminated precursor having a thickness of 3 mm.

The precursor was fired in the same way as in Example 1 to form a carbon-carbon composite. The yield of the product was 87%.

The fracture surface of the resulting carbon-carbon composite did not show a vitreous light reflection, and the matrix and the fibrous reinforcing carbon could be clearly distinguished even with unaided eyes. The composite had a flexural strength of 8.3 kg/mm² and a gas permeability of $10^{-5}$ cm²/sec.

COMPARATIVE EXAMPLE 2

This Comparative Example demonstrates that heat-treated resol fibers are unsuitable as the fibrous reinforcing material.

(A) Preparation of resol fibers

Phenol (94 g; 1 mole), 39 g (1.3 moles) of formaldehyde and 0.85 g (0.05 mole) of ammonia were mixed, and heated at 90° C. By varying the heating time, several resol resins were prepared. Each of these resol resins were subjected to a melt-spinning operation. As a result, it was found extremely difficult to melt-spin these resins, and the yield [(the weight of fibers obtained/the weight of the resin charged)×100] was 0 in most cases.

Two resol resins which seemed to have relatively good spinnability were further examined as to conditions for spinning them. Each of the two resins was spun through a spinneret having an orifice diameter of 0.2 mm at an extruding pressure of 50 cm $H_2O$ at the spinning temperatures and maximum spinning speeds shown in Table 7 to form resol fibers although in small amounts.

When these two kinds of resol fibers were heat-treated at 150° C. for 30 minutes, they were melted. Thus, when the fibers were first treated in a 20% aqueous solution of hydrochloric acid at 90° C., scrap-like cured resol fibers were formed. The characteristics of the resol fibers from which these cured resol fibers could be obtained, the behaviors of the resol resins at the time of spinning, the spinning conditions, and the properties of the cured resol fibers were determined, and the results are shown in Table 7.

(B) Preparation of a carbon-carbon composite

The cured resol fibers prepared from resin R-1 and having a higher tenacity than those prepared from R-2 resin were heat-treated in the same way as in Example 2 and cut to a length of 6 mm, and mixed by a kneader with a resol resin having a number average molecular weight of 220 and a gellation time of 140° C.×100 sec. so that the fiber content became 50% by weight. The mixture was shaped and cured in the same way as in Example 1 to form a precursor having a width of 25 mm, a thickness of 3 mm and a length of 70 mm.

The precursor was fired in the same way as in Example 1 to form a carbon-carbon composite.

The yield of the carbon-carbon composite was as low as 10%. When the fracture surface of the carbon-carbon composite was observed by a reflective microscope, it was found to be porous, and the matrix carbon and the reinforcing carbon were not fully integrated and could be clearly distinguished from each other.

The carbon-carbon composite had a gas permeability of $10^{-4}$ $cm^2$/sec. and a flexural strength of 5.5 kg/$mm^2$. Hence, the resulting carbon-carbon composite was remote from the carbon-carbon composite of the invention which has a high flexural strength and a low gas permeability.

What we claim is:

1. A carbon-carbon composite material consisting of a matrix carbon and a fibrous reinforcing carbon, said matrix carbon consisting substantially of optically anisotropic carbon and said fibrous reinforcing carbon consisting substantially of optically isotropic carbon, and said matrix carbon and fibrous reinforcing carbon forming an interface without an intervening third material, wherein said composite material has a fracture surface

Table 7

| Run No. | | R-1 | R-2 |
|---|---|---|---|
| Resol Resin | Number average molecular weight | 450 | 370 |
| | Gellation time | 150° C. × 140 sec. | 140° C. × 120 sec. |
| Spinning | Behavior at the time of spinning | At 100° C., the spinning solution had a low viscosity. At 108° C., spinning was possible for 12 seconds. At 120° C., the spinning solution foamed and gelled. (At 108° C., too, the spinning solution gelled in 10 minutes.) | At 90° C., the spinning solution had a low viscosity. At 95° C., spinning was possible for 8 seconds. At 115° C., the spinning solution foamed and gelled. (At 95° C., too, gellation occurred in 10 minutes.) |
| | Temperature (°C.) | 108–120 | 95–115 |
| | Maximum spinning speed (m/min.) | 200 | 150 |
| Properties of the cured resol fibers | Fiber diameter (microns) | 28.3 | 28.5 |
| | Tenacity (g/d) | 0.9 | 0.7 | showing a uniform vitreous light reflection produced by the method of claim 9.

2. The composite material of claim 1 in which said matrix carbon and fibrous reinforcing carbon consist substantially of amorphous carbon.

3. The composite material of claim 1 or 2 which has a broad diffraction profile at a diffraction angle of 26° when measured by an X-ray diffraction method.

4. The composite material of any one of claims 1 or 2 which has a flexural strength of at least 9 kg/mm$^2$ and a helium gas permeability of not more than $1 \times 10^{-6}$ cm$^2$/sec.

5. The composite material of any one of claims 1 or 2 which has a carbon content of at least 94% by weight.

6. The composite material of claim 5 which has a carbon content of at least 96% by weight.

7. The composite material of any one of claims 1 or 2 in which the matrix carbon and the fibrous reinforcing carbon have the same density.

8. The composite material of any one of claims 1 or 2 which when used as an anode and electrolytically etched in sulfuric acid-acidified water, develops a difference in the degree of etching between the matrix carbon and the fibrous reinforcing carbon.

9. A method for producing a carbon-carbon composite material consisting of a matrix carbon and a fibrous reinforcing carbon, which comprises heat-treating cured novolac fibers at a temperature of from 250° C. to less than 500° C. in a non-oxidizing atmosphere; shaping a resinous composition consisting of 30 to 90% by weight of the resulting heat-treated novolac fibers and 10 to 70% by weight, as the solids content after curing, of a phenolic resin; curing the shaped product; heating the cured product in a non-oxidizing atmosphere to at least 800° C. in such a manner that at least within a temperature range of 200° to 500° C., the heating is carried out at a rate of not more than 60° C. per hour; and firing the product at the final temperature reached.

10. The method of claim 9 in which the cured novolac fibers have a methylol group content of at least 3.5% by weight.

11. The method of claim 10 in which the cured novolac fibers have a methylol group content of 4 to 12% by weight.

12. The method of any one of claims 9, 10 or 11 in which the heat-treatment is carried out at a temperature of from 270° C. to 440° C.

13. The method of any one of claims 9, 10 or 11 in which the heat-treatment is carried out until in the infrared absorption spectrum of the resulting heat-treated novolac fibers, the ratio ($D_{770}/D_{1600}$) of the absorption wavelength intensity ($D_{770}$) of an absorption peak near 740 to 770 cm$^{-1}$ ascribable to adjacent hydrogen atoms on the benzene ring to the absorption wavelength intensity ($D_{1600}$) of an absorption peak near 1600 cm$^{-1}$ ascribable to the benzene ring becomes 0.05 to 0.40.

14. The method of any one of claims 9, 10 or 11 in which the resinous composition contains the resulting heat-treated novolac fibers in an amount of 50 to 80% by weight.

15. The method of any one of claims 9, 10 or 11 in which the phenolic resin is a resol resin.

16. The method of claim 9 in which the phenolic resin is a novolac resin, and the curing of the shaped resinous composition is carried out by using formaldehyde or a compound capable of liberating formaldehyde under the curing conditions.

17. The method of any one of claims 9, 10 or 11 in which the shaping and curing of the resinous composition are carried out under heat and pressure.

18. The method of any one of claims 9, 10 or 11 in which the heating of the cured product is carried out in such a manner that at least within a temperature range of 200° to 500° C., the heating is carried out at a rate of not more than 40° C. per hour.

19. The method of any one of claims 9, 10 or 11 in which the firing treatment is carried out at a temperature of at least 1,000° C.

* * * * *